US007345209B2

(12) United States Patent  
Mukhopadhyay et al.

(10) Patent No.: US 7,345,209 B2
(45) Date of Patent: Mar. 18, 2008

(54) PROCESSES FOR SYNTHESIS OF 1,3,3,3-TETRAFLUOROPROPENE

(75) Inventors: Sudip Mukhopadhyay, Williamsville, NY (US); Haridasan K. Nair, Williamsville, NY (US); Hsueh S. Tung, Getzville, NY (US); Michael Van Der Puy, Amherst, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 11/118,503

(22) Filed: Apr. 29, 2005

(65) Prior Publication Data

US 2005/0245773 A1 Nov. 3, 2005

(51) Int. Cl.
C07C 17/278 (2006.01)
C07C 17/10 (2006.01)
C07C 17/23 (2006.01)
C07C 17/25 (2006.01)
C07C 17/04 (2006.01)

(52) U.S. Cl. .................. 570/157; 570/156; 570/158; 570/175; 570/164; 570/165; 570/166; 570/167; 570/168; 570/169

(58) Field of Classification Search ............. 570/157, 570/156, 158, 175, 164, 165, 166, 167, 168, 570/169
See application file for complete search history.

(56) References Cited

U.S. PATENT DOCUMENTS

| | | | |
|---|---|---|---|
| 2,931,840 A | 4/1960 | Marquis | |
| 2,996,555 A | 8/1961 | Rausch et al. | |
| 3,472,826 A | 10/1969 | Potts et al. | |
| 3,659,023 A | 4/1972 | Regan | |
| 4,086,407 A | 4/1978 | Fozzard | |
| 4,650,914 A | 3/1987 | Woodard | 570/236 |
| 4,798,818 A | 1/1989 | Baizer et al. | |
| 4,900,874 A | 2/1990 | Ihara et al. | |
| 5,162,594 A | 11/1992 | Krespan | |
| 5,532,419 A | 7/1996 | Van Der Puy et al. | |
| 5,545,777 A | 8/1996 | Morikawa et al. | |
| 5,574,192 A | 11/1996 | VanDerPuy et al. | |
| 5,608,126 A * | 3/1997 | Morikawa et al. | 570/167 |
| 5,679,875 A | 10/1997 | Aoyama et al. | |
| 5,710,382 A | 1/1998 | Dunmead et al. | |
| 5,969,198 A | 10/1999 | Thenappen et al. | |
| 5,986,151 A * | 11/1999 | Van Der Puy | 570/175 |
| 6,023,004 A | 2/2000 | Thenappen et al. | |
| 6,031,141 A | 2/2000 | Mallikarjuna et al. | |
| 6,066,769 A | 5/2000 | Nappa et al. | |
| 6,111,150 A | 8/2000 | Sakyu et al. | |
| 6,124,510 A * | 9/2000 | Elsheikh et al. | 570/156 |
| 6,369,284 B1 | 4/2002 | Nappa et al. | |
| 6,548,719 B1 * | 4/2003 | Nair et al. | 570/157 |
| 6,809,226 B1 | 10/2004 | Pennetreau et al. | |
| 6,958,424 B1 | 10/2005 | Nair et al. | |
| 6,977,316 B1 | 12/2005 | Mukhopadhyay et al. | |
| 7,026,520 B1 | 4/2006 | Mukhopadhyay et al. | |
| 7,026,521 B1 | 4/2006 | Mukhopadhyay et al. | |
| 7,071,367 B1 | 7/2006 | Mukhopadhyay et al. | |
| 7,132,578 B1 | 11/2006 | Mukhopadhyay et al. | |
| 7,135,601 B2 | 11/2006 | Mukhopadhyay et al. | |
| 7,189,884 B2 | 3/2007 | Mukhopadhyay et al. | |
| 7,196,236 B2 | 3/2007 | Mukhopadhyay et al. | |
| 2003/0060670 A1 | 3/2003 | Nair et al. | |
| 2004/0119047 A1 | 6/2004 | Singh et al. | |
| 2005/0020862 A1 | 1/2005 | Tung et al. | |
| 2005/0080302 A1 | 4/2005 | Baker et al. | |
| 2005/0090698 A1 * | 4/2005 | Merkel et al. | 570/155 |
| 2005/0171391 A1 | 8/2005 | Janssens et al. | |
| 2007/0112227 A1 | 5/2007 | Mukhopadhay et al. | |
| 2007/0112228 A1 | 5/2007 | Mukhopadhay et al. | |
| 2007/0112229 A1 | 5/2007 | Mukhopadhay et al. | |
| 2007/0112230 A1 | 5/2007 | Mukhopadhay et al. | |
| 2007/0129580 A1 | 6/2007 | Mukhopadhay et al. | |

FOREIGN PATENT DOCUMENTS

| | | |
|---|---|---|
| EP | 0522639 | 1/1993 |
| EP | 0644173 | 3/1995 |
| EP | 729932 A1 * | 9/1996 |
| EP | 974571 A2 | 1/2000 |
| GB | 844597 | 8/1960 |
| JP | 11140002 | 5/1999 |
| JP | 2000169404 | 6/2000 |
| JP | 2000178543 | 6/2000 |
| WO | 90/08752 | 8/1990 |
| WO | 95/04021 | 2/1995 |

(Continued)

OTHER PUBLICATIONS

Banks, et al., Journal of Fluorine Chemistry, vol. 82, Issue 2, pp. 171-174 (1997).

(Continued)

Primary Examiner—Elvis O. Price
(74) Attorney, Agent, or Firm—Colleen D. Szuch

(57) ABSTRACT

Disclosed is a process for the synthesis of 1,3,3,3-tetrafluoropropene that comprises, in one preferred embodiment, providing a compound of the formula $CF_3CH_2CHFX$, wherein X is a selected from the group consisting of chlorine, bromine and iodine, and exposing said compound to reaction conditions effective to convert said compound to 1,3,3,3-tetrafluoropropene. Other processes for forming 1,3,3,3-tetrafluoropropene are also disclosed.

20 Claims, No Drawings

FOREIGN PATENT DOCUMENTS

| WO | 96/01797 A | 1/1996 |
|---|---|---|
| WO | WO 96/01797 | 1/1996 |
| WO | 98/42645 | 3/1998 |
| WO | 98/21171 | 5/1998 |
| WO | WO 98/ 21171 | 5/1998 |
| WO | 99/48993 | 9/1999 |
| WO | 00/39242 | 7/2000 |
| WO | 01/07384 | 2/2001 |
| WO | 03/027051 | 4/2003 |
| WO | 2005/012212 | 2/2005 |
| WO | 2005/042451 A | 5/2005 |
| WO | 2005/108332 | 11/2005 |
| WO | 2005/108334 | 11/2005 |
| WO | 2007/019355 A | 2/2007 |

OTHER PUBLICATIONS

Database Beilstein, Beilstein Institute For Organic Chemistry, M. Van Der Puy: J. Fluorine Chemistry, vol. 81, No. 2, 1997, pp. 187-192 XP002424669.

Database Beilstein, Beilstein Institute For Organic Chemistry, Haszeldine, Steele: J. Chem. Soc. 1953, p. 1592, 1597, XP0022424670.

Database WPI Week 199812, AN 1998-126110, XP002427152, Derwent Publications Ltd., London, GB & JP 10 007605A (Central Glass Co LTD) Jan. 13, 1998 abstract.

Database Beilstein, XP002426121.

Dickson, R.S., Fluorcarbon-Aluminum Compounds, Aust. J. Chem., 1972, 25, 761-8.

Gambareto et al., "The Reaction of chlorine monofloride with unsaturated compounds", 1976, XP00246119.

Haszeldine R.N., Free-radical Additions to Unsaturated Systems. Part XVII.[1] Reaction of Trifluoroiodomethane with Mixtures of Ethylene and Vinyl Fluoride and of Ethylene and Propene, Journal of Chemical Society, Section C: (3), 414-21. p. 415.

Henne, Albert L., et al., Chlorinated Derivatives of 2-Floropropane[1] J. American Chemical Society, Jul. 11, 1941: pp. 2692-2694, vol. 63.

J Burdon et al.: J. Fluorine Chemistry, vol. 40, pp. 283-318, XP002424668.

Knunyants, I. L. et al. Reaction of Fluoro Olefins, Institute of Heteroorganic Compounds, Bulletin of the Academy of Sciences of USSR, Division of Chemical Sciences—ISSN 0568-5230, p. 1312-1317.

Kunshenko B V et al.: Reaction of Organic Compounds with SF4-HF-Hallogenating System VII, 1992, XP002344564.

March, J. Advanced Organic Chemistry, 1997, pp. 631-636, McGraw-Hill International Book Company, XP002427150.

Vittorio Minanari, A Novel Systenis of Perhalogenated Alkenes, J. Org. Chem. 1992, 57, 5018-5019.

Haszeldine, Robert N. Et Al: Journal of the Chemical Society [Section] C: Organic, (3), 414-21, 1970, XP002343900.

\* cited by examiner

PROCESSES FOR SYNTHESIS OF 1,3,3,3-TETRAFLUOROPROPENE

FIELD OF THE INVENTION

The present invention relates to methods for the preparation of tetrafluorinated propene. More specifically, this invention concerns processes for the preparation of tetra fluoropropene in general and 1,3,3,3-tetrafluoropropene, $CF_3CH=CHF$, (HFO-1234 ze).

BACKGROUND OF THE INVENTION

Tetrafluoropropenes are known to be useful as monomers in the preparation of various homopolymers and copolymers. For example, U.S. Pat. No. 3,472,826 describes tetrafluoropropene as a co-monomer in the production of polyethylene. U.S. patent application Ser. No. 10/694,273, which is assigned to the assignee of the present invention, discloses the use of $CF_3CH=CFH$ as a refrigerant with low global warming potential and also as a blowing agent for use in connection with the formation of various types of foams. In addition, $CF_3CH=CFH$ can also be functionalized to variety of compounds useful as intermediates for making industrial chemicals.

Several methods of preparing tetrafluoropropene compounds are known. For example, U.S. Pat. No. 6,548,719 B1 describes generally the production of a wide range of fluoroolefins by dehydrohalogenating, in the presence of a phase transfer catalyst, a compound of formula $CF_3C(R^1_a R^2_b)C(R^3_c R^4_d)$ with at least one alkali metal hydroxide, where the R substituents are as defined in the patent, provided that at there is at least one hydrogen and one halogen on adjacent carbon atoms. This patent, while disclosing a process that is efficient and useful for the preparation of numerous tetrafluoropropenes, does not disclose a process specifically for the preparation of 1,3,3,3-tetrafluoropropene. Moreover, in certain applications, it may be disadvantageous to follow the requirement of this patent which requires that at there is at least one hydrogen and one halogen on adjacent carbon atoms.

The preparation of 1,3,3,3-tetrafluoropropene is disclosed in U.S. Pat. No. 5,986,151. This patent discloses a process comprising catalytic dehydrofluorination of $CF_3CH_2CF_2H$ in the gas phase to afford $CF_3CH=CHF$. The preparation of 1,3,3,3-tetrafluoropropene is also disclosed in U.S. Pat. No. 6,124,510. This patent also discloses a process comprising catalytic dehydrofluorination of $CF_3CH_2CF_2H$ in the gas phase. Each of these patents has the disadvantage of being limited to the use of 1,1,1,3,3-pentafluoropropane ("245fa") as a starting reactant, which may be undesirable for reasons of cost, availability, and/or for other reasons, such as the fact that multiple steps are frequently required to manufacture HFC-245fa.

SUMMARY OF THE INVENTION

Applicants have discovered a process for the synthesis of tetrafluoropropene in general, and particularly 1,3,3,3-tetrafluoropropene, that overcomes at least the deficiencies of the prior art noted above. The processes of the present invention in one embodiment generally comprise providing a compound of the formula (I) $CF_3CH_2CHFX$, wherein X is selected from the group consisting of fluorine, chlorine, bromine and iodine (and in preferred embodiments consisting of chlorine, bromine and iodine), and exposing said compound to reaction conditions effective to convert said compound of formula (I) to 1,3,3,3-tetrafluoropropene. For the purposes of convenience but not by way of limitation, this process is sometimes referred to herein as "the dehydrohaolgentaion process."

The processes of the present invention in another embodiment generally comprise (a) reacting a compound of the formula (I) $CHFX_2$ with a compound of the formula (II) $CH_2=CF_2$, wherein each X is independently selected from the group consisting of fluorine, chlorine, bromine and iodine, to produce a reaction product comprising a compound of formula (III) $CHXFCH_2CXF_2$, wherein X is as described above, and:and (b) exposing said compound to reaction conditions effective to convert said compound of formula (III) to 1,3,3,3-tetrafluoropropene. For the purposes of convenience but not by way of limitation, this process is sometimes referred to herein as "the addition process" since that is the first step is preferred forms of the process.

The present invention is thus directed to processes for the production of $CF_3CH=CFH$ which are amenable to scale up from readily available and relatively inexpensive starting materials.

DETAILED DESCRIPTION OF PREFERRED EMBODIMENTS

The present invention is directed to methods for the production of both the cis- and trans-isomers of 1,3,3,3 tetrafluoro-2-propene, $CF_3CH=CHF$ (hereinafter referred to collectively as "HFC-1234 ze"). For the purposes of convenience, the dehydrohalogenation process and the additions process will be described separately below.

Dehydrohalogenation Process

In preferred embodiments, the step of providing a compound of formula (I) $CF_3CH_2CHFX$, comprises: (a) reacting a compound of formula (II) $CY_4$ with a compound of formula (III) $CY_2=CY_2$, and preferably formula (III) is compound of formula $CH_2=CY_2$, wherein each Y is independently selected from the group consisting of hydrogen, fluorine, chlorine, bromine and iodine, provided that at least one Y in formula (II) is a halogen and at least one Y on a first carbon of formula III is hydrogen and that at least one Y on the other carbon of formula III is a halogen to produce a reaction product comprising a compound of formula (IV) $CY_3CH_2CHY_2$, and (b) optionally fluorinating the compound of formula (IV) under conditions effective to produce a reaction product comprising a compound of formula (I) $CF_3CH_2CHFX$.

It is contemplated that numerous and varied reaction conditions can be utilized with good effect for the reaction step (a) in view of the teachings contained herein. For example, the reaction step may comprise a liquid-phase or a gas phase reaction, either catalyzed or uncatalyzed. For liquid phase reactions, it is generally preferred that the reaction is conducted in the presence of a catalyst, preferably a ligated Cu-catalyst. The preferred ligands are amine and acetyl acetone ligands, as described in WO 9821171 A1, which is incorporated herein by reference.

The reaction (a) can be carried out in the presence of a solvent or in the absence of a solvent. Although it is contemplated that numerous reaction temperatures and pressures can be utilized for liquid phase reactions, it is generally preferred that the reaction is carried out at a temperature of from about 0° C. to about 300° C., more preferably from about 20° C. to about 250° C., and even more preferably from about 150° C. to about 250° C. The pressure of the reaction is preferably from about 5 psig to about 10 psig, and even more preferably form about 5 psig to about 6 psig.

The optional fluorination step is preferably utilized when the reaction step (a) produces a compound of the formula (IV) $CY_3CH_2CHY_2$ wherein less than four of said Y are fluorine. It is contemplated that numerous variations of fluorination conditions are effective for the purposes of the present invention, and all such conditions are within the broad scope of the invention. It is contemplated that fluorination can take place in either the gas or the liquid phase, although gas phase fluorination is generally preferred. For gas phase fluorination, it is generally preferred to utilize a catalyzed, preferably a Cr-oxide ($Cr_2O_3$) catalyzed, gas-phase fluorination at a temperature of from about 250° C. to about 500° C. in the presence HF, preferably anhydrous HF gas. In certain preferred embodiments, a flow reactor is used for the fluorination reaction. The fluorination reaction generally produces a reaction product comprising $CF_3CH_2CHFY$ and/or $CF_3CH_2CHF_2$, where Y is a halogen other than F.

After the reaction step (a) or after the optional fluorination step when either of them is used, the present invention requires exposing the compound of formula (I) $CF_3CH_2CHFX$ to reaction conditions effective to produce a reaction product comprising 1,3,3,3-tetrafluoropropene. In preferred embodiments, the exposing step comprises dehydrohalogenating the compound of formula (I). Although it is contemplated that numerous dehydrohalogenation steps can be utilized with good effect in accordance with the teachings contained herein, it is preferred in certain embodiments that this step comprises contacting the compound of formula (I) with a catalyst at a relatively elevated temperature for a time sufficient to convert the compound to 1,3,3,3-tetrafluoropropene. Certain preferred embodiments comprise introducing a stream containing the compound of formula (I) into a reactor containing catalyst, preferably a bed of iron-based catalyst, more preferably $FeCl_3$, maintained at temperature of from about 200° C. to about 400° C. and under conditions to produce a contact time of from about 2 seconds to about 30 seconds. Preferably the reaction pressure is maintained at a pressure of from about 0 psig to about 200 psig. The exposing step may also be conducted in accordance with the teachings of U.S. Pat. No. 6,548,719 B1, which is assigned to the assignee of the present invention and which is incorporated herein by reference. Gas phase dehydrofluorination with an appropriate catalyst and at elevated temperature can also be performed in accordance with the procedures as described in U.S. Pat. No. 5,986,151, which is also incorporated herein by reference.

The exposing step preferably produces a reaction product stream which comprises 1,3,3,3-tetrafluoropropene, more preferably comprises a major proportion of 1,3,3,3-tetrafluoropropene, and even more preferably comprises from about 30% to at about 60% 1,3,3,3-tetrafluoropropene.

Any by-products contained in the reaction product stream can be removed to the extent desired by known means, such as distillation etc.

One particular embodiment of the present invention involves the reaction steps set forth as Scheme 1, below:

Scheme 1

(1)

(2)

-continued

(3)

Another particular embodiment involves the addition of $CF_3X$, wherein X is a hydrogen or halogen as described above (preferably iodine or bromine), to $FHC=CH_2$, as illustrated in Scheme 2 below:

Scheme 2

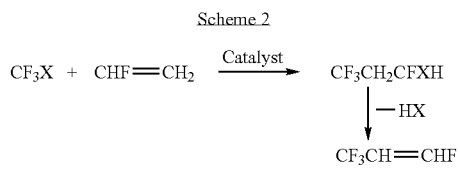

The addition reaction can be conducted in accordance with the general procedures described in Haszeldine et. al; J. Chem. Soc. 1970, (3), 414-421. As can be seen from the above, the optional fluorination step is not preferred for use in the illustrated embodiment. It should also be noted that both $CF_3CFH—CH_2X$, and $CF_3CH_2CFHX$, where X is halogen, may be formed as a result of the addition reaction in embodiments of the type disclosed in Scheme 2 and dehydrohalogenation affords HFO-1234yf and HFO-1234ze (cis- and trans-) respectively. The normal boiling point of HFO-1234yf, which is about −28° C., and HFO-1234ze, which are about −19° C. and +9° C. for trans- and cis-respectively, are sufficiently different to permit their separation by fractional distillation.

Applicants note that while $CF_3H$ is relatively unreactive; the addition of $CF_3H$ (X=H) to a fluoroolefin such as $F_2C=CF_2$ is known to occur (see *J. Fluorine Chemistry*, 2000, 102, 199-204 and WO 97022227 A1). According to certain embodiments, therefore, addition of $CF_3H$ and $CFH=CHCl$ produces two compounds, namely, $CF_3—CFH—CH_2Cl$ and $CF_3—CHCl—CFH_2$, which can then be dehydrochlorinated to produce the desired compound, namely, $CF_3CH=CFH$.

Addition Process

The step of reacting a compound of formula (I) with a compound of formula (II) is amenable to a large number of specific processing condition and steps in accordance with the teachings contained herein, and all such variations are within the broad scope of the present invention. For example, this reaction step may comprise a liquid-phase or a gas phase reaction, either catalyzed or uncatalyzed. For liquid phase reactions, it is generally preferred that the reaction is conducted in the presence of a catalyst, preferably a ligated Cu-catalyst. In preferred embodiments, the step of reacting a compound of formula (I) with a compound of formula (II) comprises a liquid-phase C—C bond formation reaction, preferably conducted at a temperature of from about 0° C. to about 200° C. and preferably in the presence of ligated Cu-catalyst. The preferred ligands are amine and acetyl acetone ligands as described in patent WO 9821171 A1, which is incorporated herein by reference. Such preferred liquid phase reactions can be conducted in the presence or absence of a solvent.

It is contemplated that numerous and varied reaction conditions other than the preferred conditions specifically disclosed herein can be utilized with good effect for the reaction step (a) in view of the teachings contained herein. Although it is contemplated that numerous reaction temperatures and pressures can be utilized for liquid phase reactions, it is generally preferred that the reaction is carried out at a temperature of from about 0° C. to about 300° C., more preferably from about 20° C. to about 250° C., and even more preferably from about 150° C. to about 250° C. The pressure of the reaction is preferably from about 1 psig to about 20 psig, and even more preferably from about 1 psig to about 10 psig.

Preferably, the step (b) of exposing a compound of the formula (III) to conditions effective to produce HFC-1234 ze comprises exposing said formula (III) compound to relatively elevated temperatures in the presence of two or more catalysts selected from the group consisting of Cr-based catalyst, Sn-based catalyst, and Fe-based catalyst. More preferably, the exposing step comprises introducing said formula (III) compound into a reactor containing a mixed catalyst reactor bed, wherein the catalyst bed comprises Cr-, Sn- and Fe-salts. In such preferred embodiments, the reactor is preferably maintained at a temperature of from about 300° C. to about 600° C., more preferably from about 350° C. to about 500° C., and even more preferably from about 450° C. to about 500° C.

Without being bound by or to any particular theory of operation, it is believed that the preferred mixed catalyst reaction scheme disclosed herein produces reaction conditions in which both fluorination and dehydrofluorination reactions occur. Thus, it is contemplated, for example, that $CF_3CH_2CF_2H$ is produced as an intermediate and/or as a byproduct as a result of a portion of the preferred mixed catalyst bed, such as Fe-salts, which promote fluorination. Furthermore, it is contemplated, without being necessarily bound to a theory of operation, that a portion of the mixed catalyst bed, such as FE-salt, promotes dehydrohalogenation of the compound (III) compound and/or fluorinated intermediates produced in the reactor, thereby enhancing the production of HFC-1234 ze.

The conditions of the preferred exposing step may be modified, particularly with regard to the dehydrofluorination reaction, in accordance with the teachings of U.S. Pat. Nos. 5,986,151 and 6,548,719 B1, each of which incorporated herein by reference.

The exposing step preferably produces a reaction product stream which comprises 1,3,3,3-tetrafluoropropene, more preferably comprises a major proportion of 1,3,3,3-tetrafluoropropene, and even more preferably comprises at least about 40% 1,3,3,3-tetrafluoropropene.

Any by-products contained in the reaction product stream can be removed to the extent desired by known means, such as distillation etc.

One particular embodiment of the present invention involves the reaction steps set forth as Scheme 3, below:

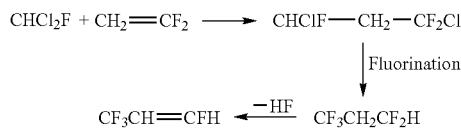

The following examples are given as specific illustrations of the invention. It should be noted that, however, that the invention is not limited to the specific details set forth in the examples. All isomers (cis and trans) of $CF_3CH=CFH$ are within the scope of the invention.

EXAMPLES

Example 1

Synthesis of $CF_3CH=CFH$ via reaction of $CF_3I$ and $CFH=CH_2$

In an autoclave, a mixture of $FHC=CH_2$ (156 mmol) and trifluoromethyliodide, $CF_3I$, (156 mmol) is heated at about 200° C. for 48 hours. The resultant reaction product comprised a mixture of compounds, including $CF_3CH_2CFHI$. The $CF_3CH_2CFHI$ is separated from the mixture and purified by distillation to afford relatively pure $CF_3CH_2CFHI$. Crown ether (18-crown-6) (0.1 mmol) and $CF_3CH_2CFHI$ (40 mmol) are added to 20 ml aq. solution of KOH (50 wt %) maintained at about 0° C. and heated to about 30-40° C. in an autoclav. The reactants in the autoclave was stirred for about 24 hours and gas chromatography of the volatile material indicates that the reaction product comprises about 75 mol % $CF_3CH=CFH$; the ratio of trans isomer to cis isomer is about 9 to 1. NMR data: $^{19}F$ ($CDCl_3$) δ=−61.3 (3F, m) and −120.0 (1F, ddq, J=77, 15, and 9 Hz) ppm for trans; −58.4 (3, dd) and −110 (1F, ddq, J=78, 37 and 16 Hz) ppm for cis.

Example 2

Synthesis of $CF_3CH=CFH$ via reaction of $CF_3Cl$ and $CFH=CH_2$

In an autoclave, a mixture of $FHC=CH_2$ (156 mmol) and trifluoromethylchloride, $CF_3Cl$, (156 mmol) and catalyst $Pd(Ph_3)_4$ (0.1 mol %) is heated at about 200° C. for 48 hours. The resultant reaction product comprised a mixture of compounds, including $CF_3CH_2CFHCl$. The $CF_3CH_2CFHCl$ is separated from the mixture and purified by distillation to afford relatively pure $CF_3CH_2CFHCl$. Crown ether (Aliquat® 336) (0.1 mmol) and $CF_3CH_2CFHCl$ (40 mmol) are added to 20 ml aq. solution of KOH (50 wt %) maintained at about 50° C. in an autoclave/pressure bottle. The mixture in the autoclave/pressure bottle is stirred for about 24 hours and gas chromatography of the volatile material indicates that the reaction product comprises about mainly greater than about 65 mol % $CF_3CH=CFH$.

Example 3

Synthesis of $CF_3CH=CFH$ via reaction of $CF_3Br$ and $CFH=CH_2$

In an autoclave, a mixture of $FHC=CH_2$ (156 mmol) and trifluoromethylbromide, $CF_3Br$, (156 mmol) and catalyst $Pd(Ph_3)_4$ (0.1 mol %) is heated at about 200° C. for 48 hours. The resultant reaction product comprised a mixture of compounds, including $CF_3CH_2CFHBr$. The $CF_3CH_2CFHBr$ is separated from the mixture and purified by distillation to afford relatively pure $CF_3CH_2CFHBr$. Tetrabutylammonium bromide (0.1 mmol) and $CF_3CH_2CFHBr$ (40 mmol) are added to 20 ml aq. solution of KOH (50 wt %) maintained at about 50° C. in an autoclave. The mixture in the autoclave is stirred for about 24 hours and gas chromatography of the volatile material indicates that the reaction product comprises about 75 mol % $CF_3CH=CFH$.

Example 4

Synthesis of $CF_3CH=CFH$ form $CCl_4$

About 2 mol of $CCl_4$ and about 1 mol of $CH_2=CHCl$ are stirred in an autoclave in the presence of about 0.005 mol of Cu-catalyst for about 6 to about 20 hours and maintained at about 20° C. to about 100° C. The reaction product mixture is separated and purified by distillation to provide a stream comprising primarily $CCl_3CH_2CHCl_2$. The $CCl_3CH_2CHCl_2$ thus produced is introduced at a flow rate of 0.05 to 0.5 lb/hr, together with about 0.1 to 1.5 lb/hr of HF, into a first catalytic reactor comprising 170 cc containing $Cr_2O_3$ or a mixture of $Cr_2O_3$ and other group-V1 metal oxides. The contact time in the reactor is from about 7 seconds to about 40 seconds and the reaction pressure is from about 5 to about 100 psig. The effluent from the reactor comprises $CF_3CH_2CHClF$, at least a portion of which is subjected to dehydrochlorination in as second catalytic reactor containing Ni-based catalysts maintained at a temperature of from about 400° C. to about 700° C. The contact time in the second reactor is from about 2 to about 30 seconds and the reaction pressure is from about 0 to about 200 psig. The effluent from the second reactor, which comprises $CF_3CH=CFH$, is then processed by low temperature distillation to provide a relatively purified product stream and providing $CF_3CH=CFH$ in an overall yield of from about 30% to about 40%.

Example 5

Synthesis of $CF_3CH=CHF$ from $CHCl_2F$ and $H_2C=CF_2$ $CHCl_2F$ (2 mol) and $CH_2=CF_2$ (1 mol) are stirred in an autoclave in the presence of 0.005 mol of Cu-catalyst for about 6 to about 20 hrs at reaction temperature of from about 20° C. to about 100° C. to produce a reaction product comprising $CHClFCH_2CClF_2$. After separation and purification as appropriate, by distillation for example, the $CHClFCH_2CClF_2$ thus obtained is passed at about 0.5 lb/hr flow rate over a mixed bed of catalyst comprising of Cr and Sn-salts at about 350° C. to about 700° C. to obtain $CF_3CH=CHF$ in an amount constituting form about 40% to about 65% over all isolated yields of $CF_3CH=CFH$.

Example 6

Synthesis of $CF_3CH=CHF$ from $CHI_2F$ and $H_2C=CF_2$ $CHI_2F$ (2 mol) and $CH_2=CF_2$ (1 mol) are stirred in an autoclave in the presence of 0.005 mol of Cu-catalyst for about 6 to about 20 hrs at reaction temperature of from about 20° C. to about 100° C. to produce a reaction product comprising $CHIFCH_2ClF_2$. After separation and purification as appropriate, by distillation for example, the $CHIFCH_2ClF_2$ thus obtained is treated with HF to afford $CF_3CH_2CHIF$ at 0-50° C. with $SbCl_5$ (5 mol %) catalyst which was passed at about 0.5 lb/hr flow rate over a mixed bed of catalyst comprising of Cr and Sn-salts at about 350° C. to about 700° C. to obtain $CF_3CH=CHF$ in an amount constituting form about 40% to about 65% over all isolated yields of $CF_3CH=CFH$.

Example 7

Synthesis of $CF_3CH=CHF$ from $CHBr_2F$ and $H_2C=CF_2$ $CHBr_2F$ (2 mol) and $CH_2=CF_2$ (1 mol) are stirred in an autoclave in the presence of 0.005 mol of Cu-catalyst for about 6 to about 20 hrs at reaction temperature of from about 20° C. to about 100° C. to produce a reaction product comprising $CHIFCH_2ClF_2$. After separation and purification as appropriate, by distillation for example, the $CHIFCH_2BrF_2$ thus obtained fluorinated with HF as in example 6 to afford $CF_3CH_2CFHBr$ and dehydrobrominated as above (example 6) to obtain $CF_3CH=CHF$. The isolated yields ranged from 40% to 65%.

Example 8

Synthesis of $CF_3CH=CHF$ from CHIBrF and $H_2C=CF_2$

CHIBrF (2 mol) and $CH_2=CF_2$ (1 mol) are stirred in an autoclave in the presence of 0.005 mol of Cu-catalyst for about 6 to about 20 hrs at reaction temperature of from about 20° C. to about 100° C. to produce a reaction product comprising $CHBrFCH_2ClF_2$. After separation and purification as appropriate, by distillation for example, the $CHBrFCH_2ClF_2$ thus obtained is passed at about 0.5 lb/hr flow rate over a mixed bed of catalyst comprising of Cr and Sn-salts at about 350° C. to about 700° C. to obtain $CF_3CH=CHF$ in an amount constituting form about 40% to about 65% over all isolated yields of $CF_3CH=CFH$.

What is claimed is:
1. A process for the synthesis of 1,3,3,3 tetrafluoropropene comprising:
   a) producing a compound having a structure according to formula (I) $CF_3CH_2CXFH$, wherein said producing involves reacting a compound of formula (II) $CF_3X$ with a compound of formula (III) $CH_2=CHY$, wherein X is a halogen other than fluorine and Y is selected from the group consisting of fluorine, chlorine, bromine and iodine, and optionally fluorinating an intermediate reaction product synthesized by said reaction; and
   b) exposing said compound of formula (I) to reaction conditions effective to convert said compound to 1,3,3,3-tetrafluoropropene.
2. The process of claim 1 wherein said reaction step a) is a liquid phase reaction.
3. The process of claim 2 wherein said reaction step a) comprises reacting said compound of formula (II) with said compound of formula (III) in the presence of a ligated Cu-catalyst.
4. The process of claim 3 wherein said ligated Cu-catalyst comprises an amine ligand.
5. The process of claim 3 wherein said ligated Cu-catalyst comprises an acetyl acetone ligand.
6. The process of claim 1 wherein the exposing step c) comprises dehydrohalogenating the compound of formula (I).
7. The process of claim 6 wherein dehydrohalogenating the compound of formula (I) comprises introducing a stream containing the compound of formula (I) into a reactor containing $FeCl_3$ catalyst.
8. The process of claim 7 wherein said reactor is maintained at temperature of from about 200° C. to about 400° C.
9. The process of claim 6 wherein said stream is introduced into said reactor under conditions to produce a contact time of from about 2 seconds to about 30 seconds.
10. The process of claim 1 wherein Y is F.
11. The process of claim 1 wherein X is bromine or iodine.
12. The process of claim 1 wherein Y is Cl.
13. A process for the synthesis of 1,3,3,3 tetrafluoropropene a) reacting a compound of the formula (I) $CHFX_2$ with a compound of formula (II) $CH_2=CF_2$, to produce a reaction product comprising a compound of formula (III) $CHXFCH_2CXF_2$, wherein each X is independently selected from the group consisting of chlorine, bromine and iodine, and wherein said reaction step (a) comprises reacting said compound of formula (I) with said compound of formula (II) in the presence of a ligated Cu-catalyst;

b) exposing said compound of formula (III) to reaction conditions effective to convert said compound to 1,3, 3,3-tetrafluoropropene.

14. The process of claim 13 wherein said exposing step comprises exposing said formula (III) compound in a reactor to two or more catalysts selected from the group consisting of Cr-based catalyst and Sn-based catalyst.

15. The process of claim 13 wherein said exposing step comprises introducing said formula (III) compound into a reactor containing a mixed catalyst reactor bed, wherein the catalyst bed comprises Cr-, Sn-salts.

16. The process of claim 15 wherein said reactor is maintained at a temperature of from about 300° C. to about 600° C.

17. The process of claim 15 wherein said exposing step comprises fluorinating said compound of formula (III) to produce a fluorinated reaction product and dehydrofluorinating said fluorinated reaction product to produce 1,3,3,3-tetrafluoropropene.

18. The process of claim 13 wherein said reaction set (a) is a liquid phase reaction.

19. The process of claim 18 wherein said ligated Cu-catalyst comprises an amine ligand.

20. The process of claim 19 wherein said ligated Cu-catalyst comprises an acetyl acetone ligand.

* * * * *